(12) United States Patent
Brown et al.

(10) Patent No.: US 9,534,965 B2
(45) Date of Patent: Jan. 3, 2017

(54) FLEXIBLE FIBRE OPTIC DEFORMATION SENSOR SYSTEM AND METHOD

(71) Applicant: University of New Brunswick, Fredericton (CA)

(72) Inventors: Anthony Brown, Fredericton (CA); Bruce Colpitts, Fredericton (CA)

(73) Assignee: University of New Brunswick, Fredericton, New Brunswick (CA)

( * ) Notice: Subject to any disclaimer, the term of this patent is extended or adjusted under 35 U.S.C. 154(b) by 0 days.

(21) Appl. No.: 14/250,057

(22) Filed: Apr. 10, 2014

(65) Prior Publication Data

US 2014/0218716 A1    Aug. 7, 2014

Related U.S. Application Data

(63) Continuation of application No. 13/122,102, filed on Apr. 26, 2011, now abandoned.

(51) Int. Cl.
| | |
|---|---|
| *G01K 11/32* | (2006.01) |
| *G01B 11/16* | (2006.01) |
| *G01L 1/24* | (2006.01) |
| *G01D 5/353* | (2006.01) |
| *G01N 21/63* | (2006.01) |

(52) U.S. Cl.
CPC ............... *G01K 11/32* (2013.01); *G01B 11/18* (2013.01); *G01D 5/35364* (2013.01); *G01D 5/35374* (2013.01); *G01L 1/242* (2013.01); *G01K 2011/322* (2013.01); *G01N 2021/638* (2013.01)

(58) Field of Classification Search
CPC ...................................................... G01K 11/32
USPC ........................................................ 356/73.1
See application file for complete search history.

(56) References Cited

U.S. PATENT DOCUMENTS

| | | | |
|---|---|---|---|
| 2003/0174924 A1* | 9/2003 | Tennyson | 385/12 |
| 2006/0200049 A1* | 9/2006 | Leo | A61B 90/06 600/587 |
| 2008/0204706 A1* | 8/2008 | Magne et al. | 356/32 |

* cited by examiner

*Primary Examiner* — Tarifur Chowdhury
*Assistant Examiner* — Omar Nixon
(74) *Attorney, Agent, or Firm* — Eugene F. Derenyi; Fogler, Rubinoff LLP

(57) ABSTRACT

A cable for distributed fiber optic sensing comprising a flexible tape, an optical fiber suitable for Brillouin scattering measurement forming at least two lengths, and at least one free end of at least one length being connectable to a reading unit, wherein at least a section of the longitudinal length of the flexible tape is situated between at least a section of the two lengths such that the two lengths are in close proximity such that a temperature gradient between the two lengths is minimized, and wherein the section of the tape and the section of lengths can flex together.

23 Claims, 5 Drawing Sheets

FLEXIBLE FIBRE OPTIC DEFORMATION SENSOR SYSTEM AND METHOD

CROSS-REFERENCE TO RELATED APPLICATIONS

This application is a continuation of U.S. application Ser. No. 13/122,102, filed on Apr. 26, 2011 (currently pending), which is incorporated herein by reference in its entirety. U.S. application Ser. No. 13/122,102 is a national stage of International Application Number PCT/CA2009/001391, filed Oct. 1, 2009 (now expired), which is incorporated herein by reference in its entirety.

FIELD

The present invention relates to measuring deformation in general and measuring deformation using Brillouin scattering in particular.

BACKGROUND

Deformation sensing can be achieved by placing point sensors across a certain range. However, this raises a problem when large engineering projects require the sensing to be done over several kilometers because numerous point sensors are required.

Conventionally, a distributed sensor is a device with a linear measurement basis, which is sensitive to a measure and at any of its points. Distributed optical fibre sensing is not well known and has been slow to be accepted into conservative large engineering projects where long sensors would be advantageous. The optical fibre is sensitive over its entire length. A single distributed optical fibre sensor can replace thousands of discrete point sensors. Traditionally, optical fibre connections were thought to be costly and troublesome. However, the cost of using fibre optics has fallen rapidly. Use of optical fibres is advantageous because they are tough, durable, stable, and can be applied in harsh environments. The fibres are also immune to electrical interference common in industrial environments and have small cross-sections, making them suitable for embedment in composite materials.

There are different types of optical fibre distributed sensors—those that measure temperature distributions by detecting Raman scattered light in a fibre, others that measure strain distributions by detecting Rayleigh scattered light, and still others that measure both temperature and strain distributions by detecting Brillouin scattered light. The sensors that are based on measurement of Brillouin scattered light include BOTDA (Brillouin Optical Time Domain Analysis), BOTDR (Brillouin Optical Time Domain Reflectometry), BOFDA (Brillouin Optical Frequency Domain Analysis) and correlation-based Brillouin distributed sensors.

A BOTDA sensor applies Brillouin Scattering, a method of detecting distributed temperature and strain using a non-linear optical effect. Generally, fibre strain and temperature are linearly associated with the frequency shift and hence the wavelength of light, caused by scattered light. Both strain and temperature cause a shift in the Brillouin frequency. The BOTDA sensor measures changes in the local strain and/or temperature conditions of an optical fibre through analysis of the Brillouin frequency of the fibre at any point. Position is determined by the round-trip transit time of the optical signal in the fibre, which is approximately 0.1 m/ns in typical fibres.

Typical fibres exhibit coefficients of change in Brillouin frequency $C_\epsilon$ 0.05 MHz per ppm change in length (microstrain, $\mu\epsilon$) and $C_T \approx 1$ MHz per ° C. change in temperature. The Brillouin frequency ($v_B$) at a point z is therefore given by:

$$v_B(z) = v_{B0}(z) + C_\epsilon \cdot \epsilon(z) + C_T \cdot T(z) \qquad \text{Eq.1}$$

where $v_{B0}(z)$ is the reference Brillouin frequency and T(z) and $\epsilon(z)$ are the local temperature and strain conditions respectively.

Typical BOTDA sensors can resolve around 1 MHz changes in Brillouin frequency resulting in a strain resolution of about 20 $\mu\epsilon$ or a temperature resolution of about 1° C. Since both temperature and strain affect the Brillouin frequency in the same way, it is normally impossible to identify which parameter has changed without further information or assumption (for instance, an assumption that the sensor is isothermal, or knowledge that the fibre is strain-free).

Some prior art sensors use a single strand of optical fibre. This is problematic since the Brillouin frequency is dependent on both local strain and temperature variables. Therefore, two strands of sensing fibre are often used in proximity of each other and placed in parallel—one detects strain and temperature, and the other detects temperature only. The fibre that detects temperature only is situated in a mechanically isolated tube to replicate a strain-free environment. Calculations of Brillouin frequency using such a set-up are inaccurate, however, since they are made with the assumption that the temperature is the same for both fibres; however, in reality, it is common for the temperatures to differ. In addition, even when the temperatures of the fibres are the same, thermal expansion of the host material will cause additional temperature-dependant strain that is not compensated for by the temperature-only fibre.

Other prior art sensors comprise at least two optical fibres in a single substrate with one of them measuring strain and temperature, and another measuring temperature only. Although this increases the likelihood that the fibres experience the same temperature conditions, thermal expansion can cause additional strain in the strain-measuring fibre that is not compensated for by the temperature-measuring fibre. In addition, these devices place the strain-sensing fibre along the neutral axis of the substrate and therefore cannot measure the curvature or displacement of the substrate itself.

SUMMARY OF THE INVENTION

This invention in one embodiment discloses an optical fibre distributed sensing apparatus that uses a cable having multiple strands of optical fibre mechanically attached longitudinally to a tape substrate.

In one embodiment of this invention, the cross-section of the cable shows a strand of fibre above and below the tape.

In another embodiment of this invention, the cross-section of the cable shows a strand of fibre on all sides of the tape.

In another embodiment of this invention, the tape is tubular and the cross-section of the cable shows multiple strands of fibres positioned equidistant from one another on the substrate. These fibres can extend longitudinally on the tape or helically around the tape to detect curvature.

A sensor according to this invention converts the raw strain measurement into curvature, displacement, or shape information over lengths which can be very long lengths. As opposed to point sensors, this invention requires only a single sensor to monitor, for example, soil or snow displacement for avalanche predictions over kilometers at one time.

Unlike in prior art BOTDA sensor systems, a tape is situated between the two fibres in accordance with one embodiment of this invention. Preferably, the tape is made of thermal conducting material such as steel, such that the difference in temperature between the two fibres is minimized; however, non-conducting tape can also be used. The temperature detected by one fibre can be subtracted from the temperature detected by the second fibre at every point across the thermal conducting substrate, which allows deformation to be detected independent of temperature. Likewise, any measurement of axial strain (i.e., pulling apart force) due to thermal expansion of the substrate can also be subtracted to remove axial strain sensitivity. Since the single strand of fibre wraps to effectively form two strands of fibre, sensitivity is doubled and two strain measurements are obtained.

Unlike strain sensors of prior art where results are obtained by analyzing and interpreting spikes on a Strain vs. Time graph, the output of the optical fibre sensor in this invention is presented in terms of displacement, which is easier to understand.

An optical fibre sensor of this invention can also be packaged in a rugged tube suitable for industrial settings and will require little expertise to install or use.

According to another embodiment, this invention relates to a cable for distributed fibre optic sensing, which includes a flexible tape that is attached to an optical fibre suitable for Brillouin scattering measurement. The optical fibre can be one strand or multiple strands forming at least two lengths that span at least a section of the longitudinal length of the flexible tape. The tape is situated between the fibre lengths, and the fibre lengths and tape flex together. The fibre lengths are in close proximity such that a temperature gradient between the two lengths is minimized. The fibre lengths may be in optical communication with each other. There is at least one free end that is connectable to a reading unit, such as a Brillouin sensor.

According to another embodiment, this invention relates to a method for measuring displacement by providing a cable having at least two lengths of optical fibre, wherein the optical fibre experiences a Brillouin effect in response to strain and temperature, introducing a first light into the first length of optical fibre such that the Brillouin effect in the optical fibre affects the first light to produce a second light, receiving the second light from the second length of optical fibre, measuring the Brillouin effect from the second light, measuring the strain and temperature from the Brillouin effect, and subtracting a measurement taken from a first point on the first length of the fibre from a measurement taken from a second point on the second length of the fibre, whereby a line drawn between the first and second point is perpendicular to a line selected from the group comprising the tangent of the curvilinear direction of the tape and the linear direction of the tape.

BRIEF DESCRIPTION

DETAILED DESCRIPTION OF THE INVENTION

Figure 1:
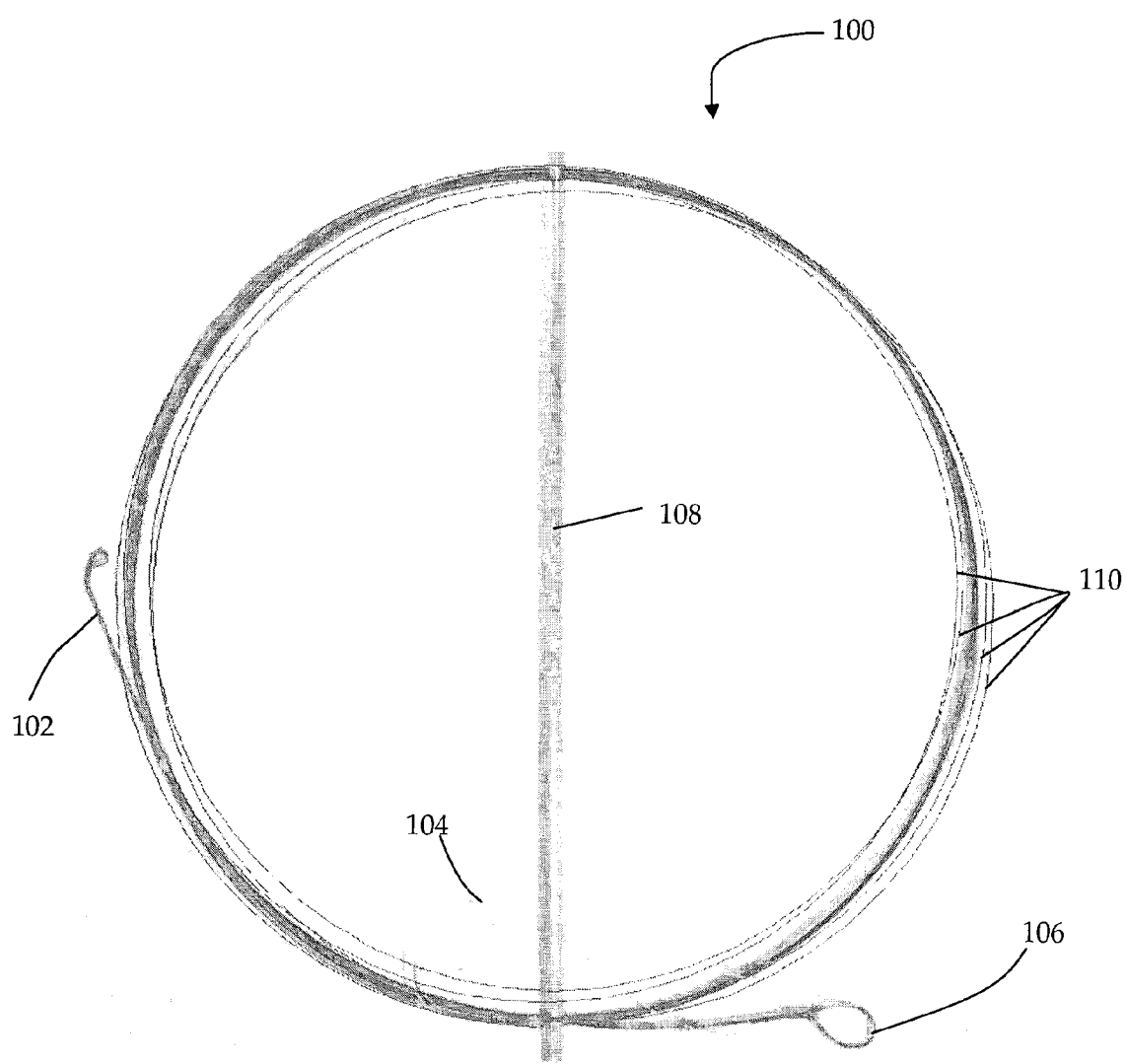
FIG. 1 is a photograph of a cable in accordance with one embodiment of the present invention.

As shown in FIG. 1, a fibre optic sensing apparatus 100 is constructed using a 12 m steel tape 102, optical fibre 104, adhesive, and conventional sensor (not shown). A length of optical fibre was bonded to both sides of the tape on the longitudinal axis, preferably using epoxy, with a turn around loop at one end 106. A BOTDA sensor, connected to the optical fibre in the conventional method, was used to measure the strain and temperature conditions of the sensing fibre. Because of the configuration of the fibre on the tape, the sensor will first measure the pass of fibre on the 'top' surface of the tape from z=0 m to z=12 m, followed by the pass on the 'bottom' of the tape from z=12 m back to z=0 m (with a small dead zone between, corresponding to the turn around loop). In FIG. 1, the tape is 12 m long for illustrative purposes. However, the length of the tape is determined and limited only by the strength of the Brillouin sensor. Using conventional Brillouin sensors, the tape can range in length from about 10 m to about 100 km. Measuring less than 10 m is possible, but is not usually cost effective. The measuring tape 108 is not part of the embodiment of the invention.

At any point z along the tape, a BOTDA measurement is made of both passes of fibre. Since the steel tape is thermally conductive and thin, the temperature will be substantially the same on both surfaces. Measurements of Brillouin frequency are taken from two points on two fibre lengths, whereby if a line were to join the two points, the line would be perpendicular to the direction of the tape and would intersect point z along the tape. By subtracting the Brillouin frequency $v_B(z)$ measured at these two points on the two fibre lengths, the terms containing $v_{B0}(z)$, $T(z)$ and any common-mode axial strain will cancel, leaving only the frequency shift due to any differential strain between the two surfaces, such as would be caused by flexure of the tape. From the differential strain measurement, the radius of curvature of the tape can be determined.

Figure 2A:
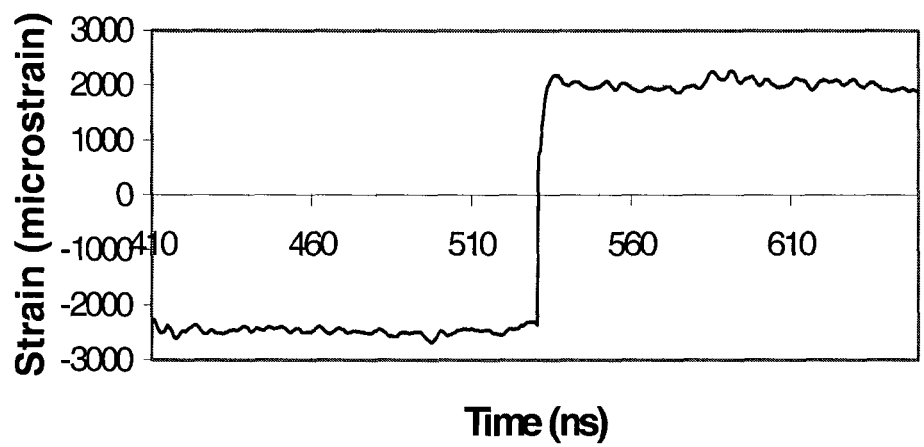
FIG. 2A is a graph of strain distribution of the circularly wrapped tape of FIG. 1.
Figure 2B:
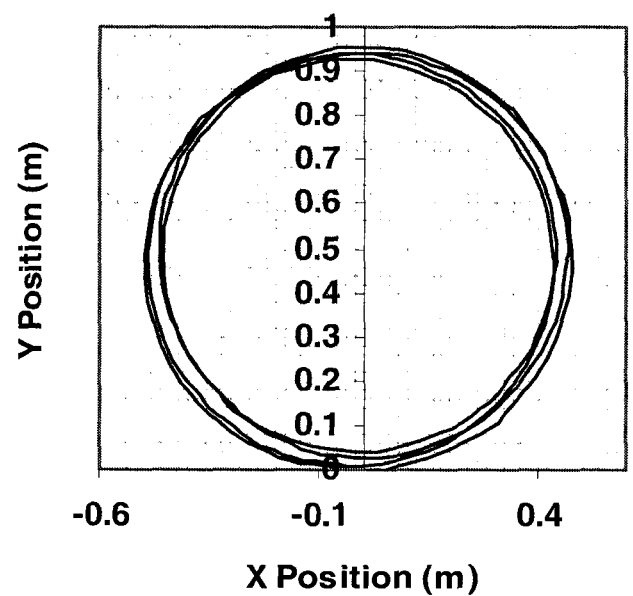
FIG. 2B is a graph of processed strain data captured from the tape of FIG. 2A.
Figure 3A:
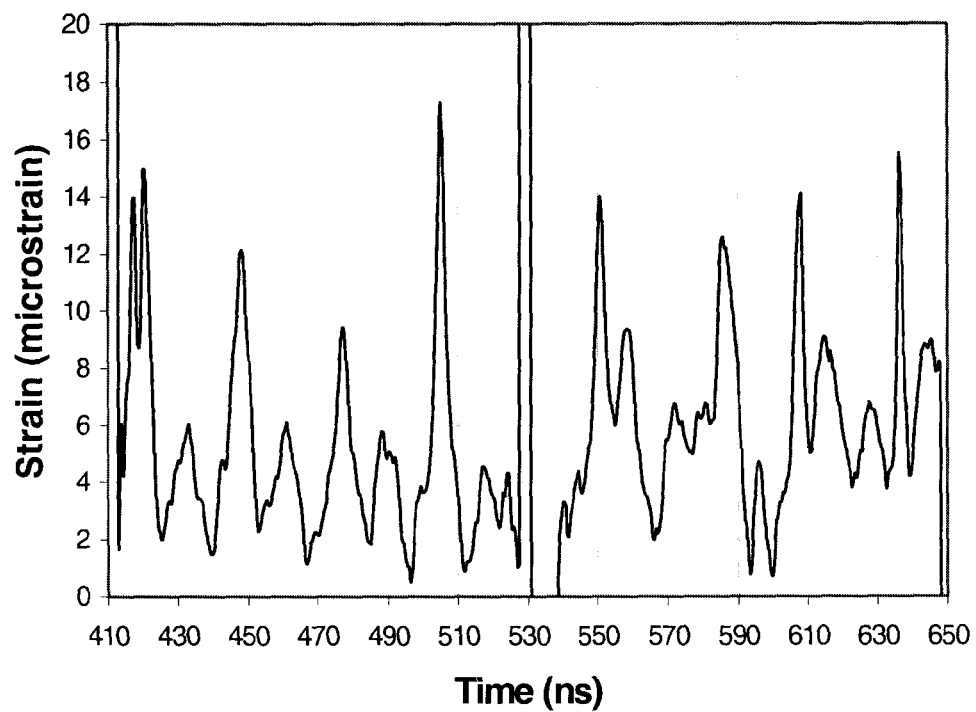
FIG. 3A is a graph of strain differential along the tape of FIG. 2A due to temperature.
Figure 3B:
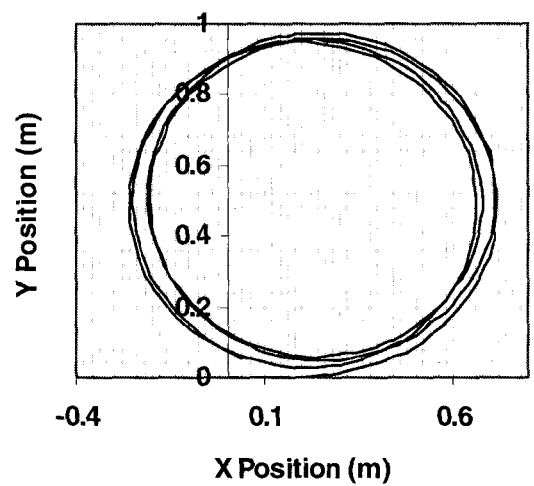
FIG. 3B is a graph of processed strain data captured from the tape of FIG. 3A.

In FIG. 1, the strain data is superimposed on the actual sensing device to show that the graph retains the same shape as the actual tape. The four thin circles of the graph 110 represent the displacement measured from each of the four loops of the tape. As in FIG. 1, the shapes of the graphs of the processed strain data in FIGS. 2B and 3B are very similar to the shape of the real tape.

Figure 4:
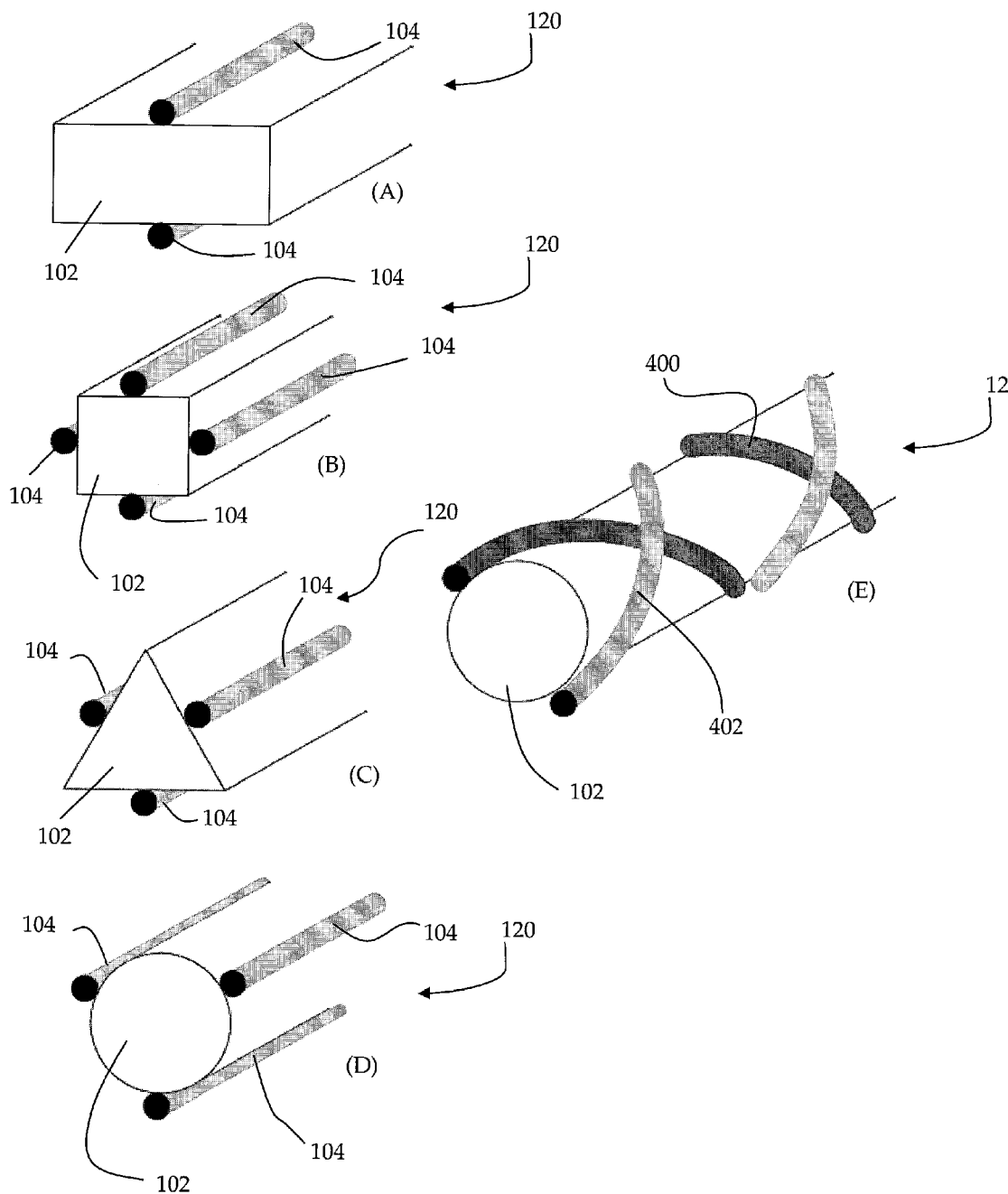
FIG. 4A is a perspective schematic of the cross-section of a cable in accordance with one embodiment of the present invention.
FIG. 4B is a perspective schematic of the cross-section of a cable in accordance with another embodiment of the present invention.
FIG. 4C is a perspective schematic of the cross-section of a cable in accordance with another embodiment of the present invention.
FIG. 4D is a perspective schematic of the cross-section of a cable in accordance with another embodiment of the present invention.
FIG. 4E is a perspective schematic of the cross-section of a cable in accordance with another embodiment of the present invention.

FIGS. 4A to 4E show five different embodiments of the invention. In FIG. 4A, strain displacement can be measured two-dimensionally on a single plane. The cable 120 comprises a tape 102 situated between two lengths of optical fibre 104. The tape 102 is attached to the two lengths 104. When the cable bends, the tape 102 bends with the lengths of fibre 104. When the cable bends on the horizontal plane, the two lengths of fibre 104 experience a different Brillouin effect in response to different strain. The fibre length at the outer curvature would experience positive strain (i.e., stretching) and the fibre length at the inner curvature would experience negative strain (i.e., compression) during flexion. The magnitude of the strain in both lengths is substantially the same as the lengths are substantially parallel. The existence of a differential strain indicates that the shape of the cable, which may be attached to an object or structure, has changed. Measuring the difference in strain between the lengths of fibre determines the magnitude of displacement.

A similar embodiment having two lengths of fibre can be designed to measure displacement on a vertical plane (not shown) by positioning the fibre lengths along the two sides of the tape rather than on the top and bottom of the tape as shown in FIG. 4A.

FIG. 4B shows another embodiment of the invention, where strain displacement can be measured three-dimensionally on both the horizontal and vertical planes. As bending occurs in the cable 120, the lengths of fibres that are diametrically opposed to each other will experience different strains occurring on one plane.

A similar embodiment (not shown) that performs the same way as the sensor design in FIG. 4B involves positioning two lengths of fibre on the top of the tape and two lengths of fibre on the bottom of the tape. When viewed in cross-section, there would be a strand of fibre at each of the four corners of a rectangular or square tape.

FIG. 4C and FIG. 4D further show other embodiments of the invention. FIG. 4C shows a cable configuration having a tape of triangular cross-section and three fibre lengths 104 extending longitudinally along at least a section of the sides of tape 102. FIG. 4D shows a cable configuration having a tape of circular cross-section and three fibre lengths 104 extending longitudinally along at least a section of the sides of tape 102. To measure data from each of the odd numbered fibre lengths, three in the exemplary embodiments shown in FIGS. 4C and 4D, a conventional sensor system that only requires access to one fibre end for measurement can be used. Single-ended sensors require access to launch one or more lights into and to receive one or more lights from one end of the fibre only. Examples of such a sensor that uses the single-ended configuration include Yokogawa's AQ8603 optical unit and Smartec's DiTeSt reading unit. Alternatively, if a sensor system that requires access to two fibre ends to launch and/or receive lights is used, then an additional fibre length can be added to make the total number of lengths an even number. This additional fibre length does not have to be used for measurement purposes, although it could be used to measure temperature only if it is suitably shielded from strain. An example of a conventional sensor that uses the dual-ended configuration is OZ Optics's Foresight™ DSTS.

FIG. 4E shows another embodiment of the invention, where only torsion (i.e., shape changes due to twisting) is measured. The fibre lengths 400 and 402 are in a helical configuration around the tape 102. A twist in the clockwise direction will compress the clockwise-wound fibre length (i.e., length 400) and tension the anti-clockwise-wound fibre length. A twist in the anti-clockwise direction will compress the anti-clockwise-wound fibre length (i.e., length 402) and tension the clockwise-wound fibre length. Axial strain or temperature changes will strain both fibre lengths equally and thus give no net result. Changes in shape due to bending will likewise tense and compress regions of both fibre lengths equally and thus produce no net result.

Another embodiment of the invention (not shown) combines two configurations—one that measures bending shape changes (i.e., FIG. 4D) and another that measures twisting shape changes (i.e., FIG. 4E). The resulting configuration would have a total of five fibre lengths comprising three lengths for t-axis bending and two lengths for differential twist.

Figure 5:
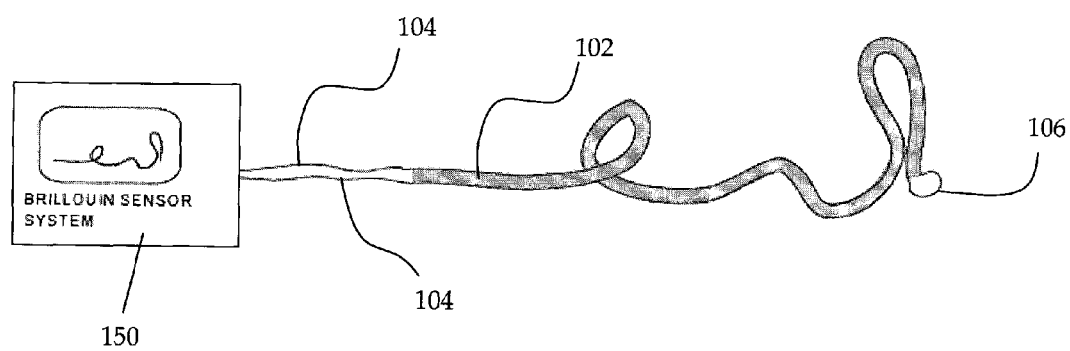
FIG. 5 is a schematic diagram of a cable in operation in accordance with one embodiment of the present invention.

FIG. 5 shows an embodiment of the invention assembled to a reading unit 450, such as a Brillouin Sensor System. The reading unit displays the shape of the optical fibre.

It would be obvious to a person of ordinary skill in the art that different fibre configurations are possible depending on a combination of factors including the number of fibre strands, the number of fibre lengths running the length of the tape, and type of reading unit used (i.e., single-ended or dual-ended systems). Fibre lengths that run along the length of the tape can be connected such that they are in optical communication or they can be separate strands. However, each separate strand would need to be attached to a reading unit.

The following non-limiting examples are illustrative of the present disclosure:

EXAMPLE #1

A 46.15 cm radius circle was made from wrapping a 12 m steel tape onto itself. Approximately four concentric circles were wrapped one on top of the other to form the circle.

Data was gathered on the circle configuration. FIG. 2A shows the strain distribution data collected over the length of the circularly wrapped tape.

As shown in FIG. 2A, a region of compression exists from 410 ns to 530 ns (located between 41.87 m and 54.13 m along the sensing fibre), and a region of tension exists from 530 ns to 650 ns (between 54.13 m and 66.38 m). This is exactly what is expected from a circular shape, since one side of the tape will be in tension, and the opposite in compression.

FIG. 2B shows the result of the processed strain data captured from the tape. The radius of the circle was determined with a measuring tape to be 46.15 cm; the average radius of curvature as measured with the sensor was 46.065 cm. This yields a 0.184% error or 0.170 cm. The standard deviation accompanying the average radius of curvature is 1.043 cm.

EXAMPLE #2

An incandescent lamp was used to heat a small portion of the tape, changing the local temperature and introducing some axial strain due to the thermal expansion of the steel. The room temperature during the experiment was 21.8° C. The temperature of the heated section varied between 50.6° C. and 53.2° C. during the data acquisition. FIG. 3A shows the difference between the tape's strain with the lamp placed on it and at room temperature. As in Example #1, the top fibre strain occurs between 410 ns and 530 ns, and the bottom fibre strain occurs between 530 ns and 650 ns. Since a shift in temperature has the same effect on the fibre Brillouin frequency as a shift in strain, periodic peaks of 'strain' were expected.

Periodic spikes are shown in the graph of FIG. 3A. The spikes occur, approximately, every 30 ns, or 300 cm. Just below 530 ns to 540 ns, there is a distortion representing the turn around at the end of the fibre. Given the radius of the circle is 46.15 cm, it is expected that the heat lamp induced 'strain' increases should occur once every circumferential length of 290 cm.

FIG. 3B shows the processed data from the heated tape. The results show the configuration of the fibres in accordance with this invention to be temperature independent. The circular shape remains despite the temperature and expansion-induced strain changes. The average radius of curvature was 45.94 cm. This yields a 0.455% error or 0.210 cm (when compared to the actual 46.15 cm radius). The standard deviation accompanying the average radius of curvature is 1.02 cm.

What is claimed is:

1. A cable for distributed fibre optic sensing comprising:
    a flexible tape;
    an optical fibre suitable for Brillouin scattering measurement forming at least two lengths, and at least one free end of at least one length being connectable to a reading unit;
    wherein at least a section of the longitudinal length of the flexible tape is situated between at least a section of the two lengths such that the two lengths are in close proximity such that a temperature gradient between the two lengths is minimized;
    wherein the section of the two lengths is not located on the neutral axis of the flexible tape; and
    wherein the section of the tape and the section of lengths can flex together, such that distributed temperature and strain in each of the lengths of fiber is detected by the reading unit from the Brillouin scattering measurements, whereby deformation of the tape is determined by subtracting the two temperature and strain measurements.

2. The cable of claim 1, wherein at least two of the total number of lengths are in optical communication.

3. The cable of claim 2, wherein the at least two lengths are formed by looping one strand of optical fibre.

4. The cable of claim 2, wherein the at least two lengths are formed by connecting at least two strands of optical fibre.

5. The cable of claim 1, wherein the at least two lengths are not in optical communication.

6. The cable of claim 1, wherein the at least two lengths are substantially parallel.

7. The cable of claim 1, wherein the flexible tape is situated between a section of two substantially parallel lengths.

8. The cable of claim 1, wherein the flexible tape is situated between a section of three substantially parallel lengths.

9. The cable of claim 1, wherein the flexible tape is situated between a section of four substantially parallel lengths.

10. The cable of claim 9, comprising first and second strands, wherein the two lengths formed by each of the first and second strands are on perpendicular axes such that flexing can be measured on two planes.

11. The cable of claim 1, wherein one length wraps helically around at least a section of the tape in a clockwise direction, and another length wraps helically around at least a section of the tape in a counter-clockwise direction such that torsion can be measured.

12. The cable of claim 1, wherein the flexible tape is situated between a section of two substantially parallel lengths and a section of two lengths forming a helical pattern in a clockwise and counter-clockwise direction such that both flexing and torsion can be measured.

13. The cable of claim 1, wherein the optical fibre is attached to the tape by an adhesive.

14. The cable of claim 1, wherein the tape has a length of about 10 m to about 100 km.

15. The cable of claim 1, wherein the tape is made of a thermally conductive material.

16. The cable of claim 1, wherein the tape is made of a non-conductive material.

17. The cable of claim 1, wherein the optical fibre is embedded in the tape.

18. A fiber optic deformation sensor system comprising a cable for distributed fibre optic sensing comprising:
    a flexible tape;
    an optical fibre suitable for Brillouin scattering measurement forming at least two lengths, and at least one free end of at least one length being connectable to a reading unit;
    wherein at least a section of the longitudinal length of the flexible tape is situated between at least a section of the two lengths such that the two lengths are in close proximity such that a temperature gradient between the two lengths is minimized;
    wherein the section of the two lengths is not located on the neutral axis of the flexible tape; and
    wherein the section of the tape and the section of lengths can flex together, wherein the cable is connected to a reading unit, such that distributed temperature and strain in each of the lengths of fiber is detected by the reading unit from the Brillouin scattering measurements, whereby deformation of the tape is determined by subtracting the two temperature and strain measurements.

19. The system of claim 18 wherein the reading unit is a Brillouin sensor in optical communication with the optical fibre for measuring strain and temperature.

20. The system of claim 19, wherein the Brillouin sensor is a single-ended sensor.

21. A method for measuring deformation comprising the steps of:
    (a) providing at least two lengths of optical fibre;
    (b) passing at least one light through the at least two lengths of fibre causing Brillouin scattering in each of the lengths of fibre;
    (c) measuring Brillouin scattering in each of the lengths of fibre;
    (d) detecting distributed temperature and strain in each of the lengths of fibre from the Brillouin scattering measurements; and
    (e) subtracting the temperature and strain measurements to determine deformation.

22. The method of claim 21, wherein the deformation measurement is a measurement of curvature of the at least two lengths of optical fibre.

23. The method of claim 21, wherein the optical fibre has a length of about 10 m to about 100 km.

* * * * *